United States Patent
Andreoni et al.

(10) Patent No.: US 6,844,087 B1
(45) Date of Patent: Jan. 18, 2005

(54) MATERIAL FOR USE IN A LIGHT-EMITTING DEVICE AND HIGHLY EFFICIENT ELECTROLUMINESCENT DEVICE

(75) Inventors: Wanda Andreoni, Gattikon (CH); Alessandro Curioni, Gattikon (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/614,511

(22) Filed: Jul. 11, 2000

(30) Foreign Application Priority Data

Jul. 12, 1999 (EP) .............................................. 99113398

(51) Int. Cl.$^7$ ........................ H05B 33/14; C07D 215/00
(52) U.S. Cl. ...................... 428/690; 428/704; 428/917; 313/504; 313/506; 252/301.16; 252/301.26; 546/152; 546/153; 546/159; 546/170; 546/172; 257/40; 257/103
(58) Field of Search .................................. 428/690, 704, 428/917; 313/504, 506; 252/301.16, 301.26; 546/152–153, 159, 170, 172; 257/40, 103

(56) References Cited

U.S. PATENT DOCUMENTS

| | | | | |
|---|---|---|---|---|
| 4,885,211 A | * | 12/1989 | Tang et al. | 428/457 |
| 5,382,477 A | * | 1/1995 | Saito et al. | 428/690 |
| 5,484,922 A | * | 1/1996 | Moore et al. | 546/7 |
| 5,597,925 A | * | 1/1997 | Ohta et al. | 548/145 |
| 5,709,959 A | * | 1/1998 | Adachi et al. | 428/690 |

* cited by examiner

*Primary Examiner*—Deborah Jones
*Assistant Examiner*—Ling Xu
(74) *Attorney, Agent, or Firm*—Ference & Associates

(57) ABSTRACT

A material is provided that can be used for a light-emitting device. The base unit of said material is tris(8-quinolinolato) aluminum(III) (Alq3). This Alq3 is substituted in the said 3- or 4-position with an electron-donor group and simultaneously in the said 5-position with an electro-acceptor or p-delocalizing group. Using this material as an emitting luminescent layer, the efficiency of the intrinsic luminescence can be greatly enhanced.

11 Claims, No Drawings

MATERIAL FOR USE IN A LIGHT-EMITTING DEVICE AND HIGHLY EFFICIENT ELECTROLUMINESCENT DEVICE

FIELD OF THE INVENTION

The present invention relates generally to a material for use in a light-emitting device, and more particularly to increasing the efficiency of organic light-emitting devices (OLEDs).

BACKGROUND OF THE INVENTION

Electroluminescent devices based on organic thin layers are light-emitting devices similar to semiconductor-based light-emitting diodes, and are currently being considered for the next generation of flat panel displays. Structurally, these devices contain spaced electrodes separated by an electroluminescent medium which emits light in response to the application of an electrical potential difference across the electrodes.

Preferred forms of OLEDs typically include an anode, an organic hole injecting and transporting zone in contact with the anode, an electron injecting and transporting zone forming a junction with the organic hole injecting and transporting zone, and a cathode in contact with the electron injecting and transporting zone. By application of an electric potential across the electrodes, holes and electrons are injected into the organic zones from the anode and cathode, respectively. Light emission results from the hole-electron recombination within the subject device. This carrier recombination generates excited molecules, which eventually emit light or become thermally deactivated. The efficiency of present OLEDs is thus highly dependent upon both carrier recombination efficiency and photoluminescence quantum yield of the emitting material.

In OLEDs based on small molecules, one of the common electroluminescent units is a highly flourescent aluminum complex, tris(8-quinolinolato)aluminum(III) (Alq3). This flourescent aluminum complex (Alq3) emits a green light and fulfills a number of prerequisites, including but not limited to, when used the device is stable and is quite suitable for carrier transport. The luminescence yield, however, is relatively low. Attempts to improve the luminescence yield have been made by doping the Alq3 layer with fluorescent dye molecules.

Kido et al., Appl. Phys. Lett., vol. 73, no. 19, pages 2721–2723, dated Nov. 9, 1998, discloses an efficient organic electroluminescent device which is fabricated by using tris(4-methyl-8-quinolinolato)aluminum(III) (Almq3) as an emitter layer. Additionally, to using this complex, a multi-layer device structure consisting of a hole-injecting layer, a hole transport layer, a dye-doped Almq3 emitting layer, and an electron transport layer was employed in order to reduce the driving voltage as well as to maximize carrier recombination efficiency. Kido et al. reports a maximum luminescence of over 140 000 cd/m$^2$ and an external quantum efficiency of 7.1%, which is believed to be the highest efficiency ever reported for organic devices.

U.S. Pat. No. 5,150,006, discloses an internal junction organic electroluminescent device comprised of, in sequence, an anode, an organic hole injecting and transporting zone, an organic electron injecting and transporting zone, and a cathode. The organic electron injecting and transporting zone is comprised of an electron injecting layer in contact with the cathode. Interposed between the electron injecting layer and the organic hole injecting and transporting zone is a blue emitting luminescent layer comprised of an aluminum chelate containing a phenolato ligand and two $R^s$-8-quinolinolato ligands, where $R^s$ substituents are used to block the attachment of more than two substituted 8-quinolinolato ligands to the aluminum atom. The presence of the phenolato ligand shifts the device emission to the shorter blue wavelengths of the spectrum and increases emission efficiency. Increased operating stability can be realized by the incorporation of a pentacarboxyclic aromatic fluroescent dye.

U.S. Pat. No. 5,456,988 discloses an electroluminescent (EL) device including an organic electron transport layer comprising Alq3 substituted with Cl or Br in the 5-position. A useful EL device is provided that has excellent durability and retains stable luminescence for a long period of time by using a compound other than the 8-quinolinolato-aluminum complex as an emitting material. No values of luminescence for the single halogen substitution, however, are reported.

A need has thus been recognized to enhance the luminescence of OLEDs.

SUMMARY OF THE INVENTION

The present invention, in accordance with at least one presently preferred embodiment, exploits an organic material having tris(8-quinolato)aluminum(III) (Alq3) as a base unit. Consequently, the present invention broadly contemplates use of an organic material in light-emitting devices to increase intrinsic luminescence of the organic molecular unit.

In one aspect of the present invention, there is provided a Alq3-based material in which the intrinsic luminescence of the organic molecular unit is directly enhanced by a modification to the relevant electron states, preferably through specific substitutions on the quinolate ring, namely by substituting the Alq3 unit in positions 3 or 4 and 5. An electron-donor group is substituted in the 3- or 4-position and an electron-acceptor or p-delocalizing group is substituted in the 5-position, preferably simultaneously. The combined substitution amplifies the enhancement of the luminescence and reduces the induced shift of the ionization potential and electronic affinity values with respect to single substitutions which is important to incorporate the new compounds in available device structures.

In another aspect of the present invention, an electroluminescent device is provided which comprises an anode, an organic hole injecting and transporting zone, an organic electron injecting and transporting zone, a cathode and a luminescent layer of tris(8-quinolinolato)aluminum(III) (Alq3), wherein said Alq3 is substituted in the 3- or 4-position with an electron-donor group and simultaneously substituted in said 5-position with an electron-acceptor or a p-delocalizing group.

For a better understanding of the present invention, together with other and further features and advantage thereof, reference is made to the following description, and the scope of the invention will be pointed out in the appended claims.

DETAILED DESCRIPTION OF THE PREFERRED EMBODIMENTS

Formula I shows Alq3 and the location of the atoms on the quinolinolato ligand labeled with the standard notation.

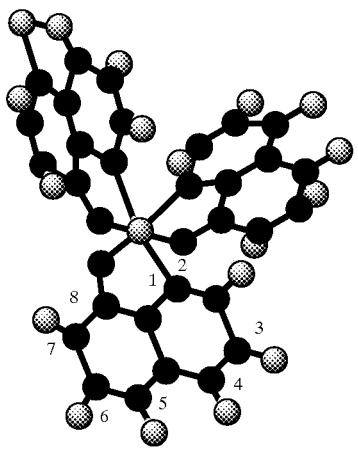

Formula I

The relatively weak (compared with other fluorescent organic materials) luminescence of the Alq3 molecule is associated with different spatial localization of the electron states involved in the luminescence process which limits the corresponding transition probability. Specifically, the holes acceptor states (Highest Occupied Molecular Orbital (HOMO) set of states) are localized mainly in the phenoxyde side of the ligands whereas the electron acceptor states (Lowest Unoccupied Molecular Orbital (LUMO) set of states) are localized mainly on the pyridyl side of the ligands. HOMO-LUMO electronic transitions (the relevant ones for luminescence properties) are thus limited.

An increase in the intrinsic luminescence yield can be achieved by modifying the relevant electron states by means of specific chemical substitutions on the quinolate rings which improve the spatial overlap between the HOMO and LUMO set of states, and therefore, indirectly the transition probability and hence the intrinsic luminescence yield. In accordance with the present invention, substitutions are made using an electron-donor group ($R^{py}$) in the 3- or 4-position and, at the same time, an electron-acceptor or p-delocalizing group ($R^{ph}$) in the 5-position.

The substituents $R^{py}$ are preferably selected from the groups —CR'R"R'", —NRR' and —O—R, wherein R, R', and R"=(H, Alkyl), R'"=(Alkyl), and may be generally selected from any group that is able "to push" electrons onto the ligands.

An electroluminescent device using the Alq3 derivatives of the present invention preferably consists of a hole injection electrode, an electron injection electrode and at least one organic emitting layer incorporating at least one of the proposed Alq3 derivatives. It should be understood that the electroluminescent device may contain additional hole-transport layers between the hole injection layer and the organic emitting layers and/or additional electron transport layers between the electron injection electrode and the organic light-emitting layers.

It is to be further understood that since the organic light-emitting layer consists of Alq3 derivatives having a larger intrinsic luminescence yield with a calculated enhancement factor up to four, the device will have a larger quantum efficiency than any other device made by unsubstituted and undoped Alq3. Moreover, since this is obtained by directly modifying the Alq3 molecule and without adding any highly fluorescent dopants, all contrary to the work known from the prior art, the good stability and carrier transport properties of the Alq3 layers are preserved, and no additional energy transfer step from Alq3 to the dopant molecules is needed to have high luminescence yield.

If not otherwise stated herein, it is to be assumed that all patents, patent applications, patent publications and other publications mentioned and cited herein are hereby fully incorporated by reference herein as if set forth in their entirety herein.

Although illustrative embodiments of the present invention have been described herein with reference to the accompanying drawing, it is to be understood that the invention is not limited to those precise embodiments, and that the various other changes and modifications may be affected therein by one skilled in the art without departing from the scope or spirit of the invention.

What is claimed is:

1. An organic material having tris (8-quinolinato) aluminum(III) (Alq3) as a base unit and wherein said Alq3 is substituted in positions selected from the group consisting of the 3-, 4- and 5-positions and wherein:
    said 3- or 4-position is substituted with a group consisting of an electron-donor group; and
    said 5-position is substituted with a group consisting of an electron-acceptor and p-delocalizing group and said 3- or 4-position substitution occurs simultaneously with said 5-position substitution.

2. The material according to claim 1, wherein said electron-donor group in said 3- or 4-position is selected from a group consisting of —CR'R"R'", $NR_2$, and —OR, wherein R, R', R"=H or Alkyl, and R'"=Alkyl.

3. The material according to claim 1, wherein said electron-acceptor or p-delocalizing groups in the said 5-position are selected from a group consisting of —$CX_3$, —$CX_2$, —$CX_3$, —$SO_3R$, —CR=$CR_2$, —CX=$CX_2$, —COOR, —$SO_3R$, —$SO_3M$ and —COOM, whereby X=F, Cl, Br; R=H or Akyl, and M=metal ion.

4. The material according to claim 2, wherein said electron-acceptor or p-delocalizing groups in said 5-position are selected from a group consisting of —$CX_3$, —$CX_2$, —$CX_3$, —$SO_3R$, —CR=$CR_2$, —CX=$CX_2$, —COOR, —$SO_3R$, —$SO_3M$ and —COOM, whereby X=F, Cl, Br; R=H or Akyl, and M=metal ion.

5. The material according to claim 1, wherein said electron-donor group in the said 3- or 4-position is —$CH_3$ and said electron-acceptor group in the said 5-position is —$CF_3$.

6. The material according to claim 1, wherein said electron-donor group in said 3- or 4-position is —OR and said electron-acceptor group in said 5-position is —CF=$CF_2$.

7. The material according to claim 1, wherein said electron-donor group in the said 3- or 4-position is —$CH_3$ and said electron-acceptor group in said 5-position is —CF=$CF_2$.

8. An electroluminescent device comprising:
    an anode,
    an organic hole injecting and transporting first layer,
    an organic electron injecting and transporting second layer;
    a cathode and
    a luminescent third layer of tris(8-quinolinolato) aluminum(III) (Alq3), wherein said Alq3 is substituted in positions selected from the group consisting of the 3- and 5-positions wherein the 3- or 4-position is substituted with a group consisting of an electron-donor group and simultaneously substituted in said 5-position with a group consisting of an electron-acceptor and a p-delocalizing group.

9. An electroluminescent device according to claim 8, wherein said electron-donor group in the 3- or 4-positions is selected from the group consisting of —CR'R"R'", NR$_2$, and —OR, wherein R, R', R"=H or Alkyl and R'"=Alkyl.

10. An electroluminescent device according to claim 8, wherein said electron-donor or p-delocalizing groups in the 5-position are selected from the group consisting of —CX$_3$, —CX$_2$, —CX$_3$, —SO$_3$R, —CR=CR$_2$, —CX=CX$_2$, —COOR, —SO$_3$M, and —COOM, whereby X=F, Cl, Br; R=H or Alkyl and M=metal ion.

11. An electroluminescent device according to claim 9, wherein said electron-donor or p-delocalizing groups in the 5-position are selected from the group consisting of —CX$_3$, —CX$_2$, —CX$_3$, —SO$_3$R, —CR=CR$_2$, —CX=CX$_2$, —COOR, —SO$_3$M, and —COOM, whereby X=F, Cl, Br; R=H or Alkyl and M=metal ion.

* * * * *